US010712329B2

(12) United States Patent
Smith, III et al.

(10) Patent No.: US 10,712,329 B2
(45) Date of Patent: Jul. 14, 2020

(54) METHODS OF MEASURING METAL POLLUTANTS ON SKIN

(71) Applicant: The Procter & Gamble Company, Cincinnati, OH (US)

(72) Inventors: Edward Dewey Smith, III, Mason, OH (US); Jessa Leigh Meyers, Cincinnati, OH (US); Jennifer Lynn Morgan, Deerfield Township, OH (US); Casey Patrick Kelly, Wyoming, OH (US); Andrei Sergeyevich Shauchuk, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 69 days.

(21) Appl. No.: 16/027,006

(22) Filed: Jul. 3, 2018

(65) Prior Publication Data

US 2019/0137470 A1    May 9, 2019

Related U.S. Application Data

(60) Provisional application No. 62/528,294, filed on Jul. 3, 2017.

(51) Int. Cl.
| | |
|---|---|
| *G01N 33/20* | (2019.01) |
| *G01N 1/02* | (2006.01) |
| *G01N 1/28* | (2006.01) |
| *A61B 10/02* | (2006.01) |
| *A61B 5/00* | (2006.01) |
| *G01N 1/40* | (2006.01) |
| *C12M 1/34* | (2006.01) |

(52) U.S. Cl.
CPC ............. *G01N 33/20* (2013.01); *A61B 5/443* (2013.01); *A61B 10/02* (2013.01); *G01N 1/02* (2013.01); *G01N 1/28* (2013.01); *G01N 1/4044* (2013.01); *A61B 5/6833* (2013.01); *G01N 2001/028* (2013.01); *G01N 2001/2833* (2013.01)

(58) Field of Classification Search
CPC ....... A61B 10/02; A61B 5/443; A61B 5/6833; G01N 1/02; G01N 1/28; G01N 1/4044; G01N 2001/028; G01N 2001/2833; G01N 33/20
See application file for complete search history.

(56) References Cited

U.S. PATENT DOCUMENTS

| | | |
|---|---|---|
| 5,140,986 A | 8/1992 | Klingner |
| 8,119,168 B2 | 2/2012 | Johnson et al. |
| (Continued) | | |

FOREIGN PATENT DOCUMENTS

| | | |
|---|---|---|
| CN | 104820010 B | 3/2017 |
| JP | 2011107113 A | 6/2011 |
| (Continued) | | |

OTHER PUBLICATIONS

Jurij Hostynek et al: "Human Stratum Corneum Penetration by Nickel", Acta Derm Venereal, Dec. 31, 2001 (Dec. 31, 2001), pp. 5-10. (Year: 2001).*

(Continued)

*Primary Examiner* — Jennifer Wecker

(57) ABSTRACT

A method for measuring an airborne metal pollutant on skin can include the taking of a skin sample and measuring of a target metal utilizing inductively coupled plasma tandem mass spectrometry.

10 Claims, 4 Drawing Sheets

(56) References Cited

U.S. PATENT DOCUMENTS

| | | | |
|---|---|---|---|
| 8,685,908 | B2 | 4/2014 | Smith, III, et al. |
| 8,795,695 | B2 | 8/2014 | Smith, III |
| 9,901,584 | B2 | 2/2018 | Wei |
| 10,183,298 | B2 | 1/2019 | Walling |
| 10,201,481 | B2 | 2/2019 | Smith, III |
| 10,450,537 | B2 | 10/2019 | Salvador |
| 2002/0019055 | A1 | 2/2002 | Brown |
| 2012/0219610 | A1 | 8/2012 | Smith, III et al. |
| 2013/0045248 | A1 | 2/2013 | Coffindaffer et al. |
| 2013/0045263 | A1 | 2/2013 | Smith, III et al. |
| 2013/0045284 | A1 | 2/2013 | Stella |
| 2013/0045285 | A1 | 2/2013 | Stella |
| 2013/0045907 | A1 | 2/2013 | Lanzalaco |
| 2013/0045961 | A1 | 2/2013 | Smith, III et al. |
| 2015/0250697 | A1 | 9/2015 | Smith, III et al. |
| 2015/0251222 | A1 | 9/2015 | Walling |
| 2015/0377751 | A1* | 12/2015 | Wehmeyer .............. A61B 5/443 436/96 |
| 2016/0074300 | A1 | 3/2016 | Salvador et al. |
| 2018/0133711 | A1* | 5/2018 | Funk ................ A61B 5/150022 |

FOREIGN PATENT DOCUMENTS

| | | |
|---|---|---|
| JP | 2012098097 A | 5/2012 |
| WO | WO2012135227 A2 | 10/2012 |
| WO | WO2018049556 A1 | 3/2018 |
| WO | WO2018049557 A1 | 3/2018 |
| WO | WO2018049558 A1 | 3/2018 |
| WO | WO2018050056 A1 | 3/2018 |

OTHER PUBLICATIONS

U.S. Appl. No. 16/352,413, filed Mar. 13, 2019, Karl Shiqing Wei et al.

Batkin et al., Mathematical analysis of dermal absorption rate of heavy metals, Conf Proc IEEE Eng Med Biol Soc. (2015), pp. 8066-8069 I I.

Beriro et al., A review of the current state of the art of physiologically-based tests for measuring human dermal in vitro bioavailability of polycyclic aromatic hydrocarbons (PAH) in soil, Journal of Hazardous Materials 305 (2016), pp. 240-259.

Bordignon et al., Nickel, palladium and rhodium induced IFN-gamma and IL-10 production as assessed by in vitro ELISpot-analysis in contact dermatitis patients, BMC Immunology 2008, 9:19.

C. Stuart Baxter, Joseph D. Hoffman, Michael J. Knipp, Tiina Reponen& Erin N. Haynes (2014) Exposure of Firefighters to Particulates and Polycyclic Aromatic Hydrocarbons, Journal of Occupational and Environmental Hygiene, 11:7, D85-D91, DOI:10.1080/15459624.2014.890286.

Chen et al., Assessing inhalatory and dermal exposures and their resultant health-risks for workers exposed to polycyclic aromatic hydrocarbons (PAHs) contained in oil mists in a fastener manufacturing industy, Environment International vol. 34 (2008), pp. 971-975.

du Plessis, Assessment of dermal exposure and skin condition of refinery workers exposed to selected metals, thesis submitted for the degree Philosophiae Doctor in Occupational Hygieneat the Potchefstroom Campus of the North-West University, Jul. 2010.

Gawkrodger et al., Nickel skin levels in different occupations and an estimate of the threshold for reacting to a single open application of nickel in nickel-allergic subjects, British Journal of Dermatology vol. 166, Issue 1, Jan. 2012, pp. 82-87.

Hession et al., Measurement of contaminant removal from skin using a portable fluorescence scanning system, Journal of Environmental Radioactivity 85 (2006), pp. 196-204.

Hostynek et al., Human Stratum Corneum Penetration by Nickel, Acta Derm Venereol, Suppl 212, pp. 5-10, Dec. 31, 2001.

Hughson et al., Characterization and Assessment of Dermal and Inhalable Nickel Exposures in Nickel Production and Primary User Industries, Ann. Occup. Hyg., vol. 54, No. 1 (2010), pp. 8-22.

Imbert et al., Development of an integrated evaluation platform to study the impact of urban pollution on skin and identify future protective strategies, Journal of Investigative Dermatology (2015), vol. 135, Epidermal structure and function 291, S50.

International Search Report and Written Opinion of the International Searching Authority, PCT/US2018/040664, dated Oct. 5, 2018, 10 pages.

Julander et al., Nickel deposited on the skin—visualization by DMG test, Contact Dermatitis, 64, 2011, pp. 151-157.

Kammer et al., Evaluation of a tape-stripping technique for measuring dermal exposure to pyrene and benzo(a) pyrene, Journal of Environmental Monitoring, 2011, 13, pp. 2165-2171.

Kang-Sickel et al., Detection of Naphthalene Keratin Adducts in Human Skin using ELISA, Conference Paper Abstract, Drug Metabolism Reviews, 14th North American Regional international society for the study of xenobiotics Meeting, Jan. 2006.

Kang-Sickel et al., S-Arylcysteine--Keratin Adducts as Biomarkers of Human Dermal Exposure to Aromatic Hydrocarbons, Chem. Res. Toxicol. 2008, vol. 21, No. 4, pp. 852-858.

Lai et al., Heavy metals and hand dermatitis: analysis of data in the US National Health and Nutrition Examination Survey, International Journal of Dermatology 2016, 55, e114-e115.

Lefebvre et al., Consequences of urban pollution upon skin status. A controlled study in Shanghai area, International Journal of Cosmetic Science, 2016, vol. 38, pp. 217-223.

Lefebvre et al., Evaluation of the impact of urban pollution on the quality of skin: a multicentre study in Mexico, International Journal of Cosmetic Science, 2015, 37, pp. 329-338.

Lehner et al., Detection of hazardous polycyclic aromatic hydrocarbons (PAH) in black tattooed human skin and lymph nodes, Experimental Dermatology, 2012, 21, e49, P293.

Liden et al., Assessment of skin exposure to nickel, chromium and cobalt by acid wipe sampling and ICP-MS, Contact Dermatitis vol. 54, 2006, pp. 233-238.

Liden et al., Deposition of nickel, chromium, and cobalt on the skin in some occupations—assessment by acid wipe sampling, Contact Dermatitis vol. 58, 2008, pp. 347-354.

Magnani et al., Skin Damage Mechanisms Related to Airborne Particulate Matter Exposure, Toxicological Sciences (2016), 149(1), 227-236.

Mark Boeniger, Charles Neumeister & Angela Booth-Jones (2008) Sampling and Analytical Method Development and Hand Wipe Measurements of Dermal Exposures to Polycyclic Aromatic Hydrocarbons, Journal of Occupational and Environmental Hygiene, 5:7, 417-425, DOI: 10.1080/15459620802111319.

Mavrofrydi et al., Comparative Assessment of HIF-1 and Akt Responses in Human Lung and Skin Cells Exposed to Benzo[]pyrene: Effect of Conditioned Medium from Pre-exposed Primary Fibroblasts, Environmental Toxicology vol. 31, Issue 9, Sep. 2016, pp. 1103-1112.

N. Bartsch, J. Heidler, B. Vieth, C. Hutzler & A. Luch (2016) Skin permeation of polycyclic aromatic hydrocarbons: A solvent-based in vitro approach to assess dermal exposures against benzo[a]pyrene and dibenzopyrenes, Journal of Occupational and Environmental Hygiene, 13:12, 969-979, DOI: 10,1080/15459624.2016.120074.

Nishikawa et al., Further evaluation of the skin micronucleus test: Results obtained using 10 polycyclic aromatic hydrocarbons, Mutation Research/Genetic Toxicology and Environmental Mutagenesis, vol. 588 (2005), pp. 58-63.

Oh et al., Dermal Exposure Assessment of Heavy Metal in Children's Products, Epidemiology: Jan. 2011—vol. 22—Issue 1—p. S284.

Richard P. Moody, Andrey V. Tytchino, Anna Yip & Sanya Petrovic (2011) A Novel "By Difference" Method for Assessing Dermal Absorption of Polycyclic Aromatic Hydrocarbons from Soil at Federal Contaminated Sites, Journal of Toxicology and EnvironmentalHealth, Part A, 74:19, 1294-1303, DOI: 10.1080/15287394.2011.589104.

Scheepers et al., The occupational exposure of dermatology nurses to polycyclic aromatic hydrocarbons—evaluating the effectiveness of better skin protection, Scandinavian Journal of Work, Environment & Health 2009;35(3):212-221.

(56) References Cited

OTHER PUBLICATIONS

Sobus et al., Comparing Urinary Biomarkers of Airborne and Dermal Exposure to Polycyclic Aromatic Compounds in Asphalt-Exposed Workers, Ann. Occup. Hyg., vol. 53, No. 6 (2009), pp. 561-571.
Soeur et al., Photo-pollution stress in skin: Traces of pollutants (PAH and particulate matter) impair redox homeostasis in keratinocytes exposed to UVA1, Journal of Dermatological Science 86 (2017) pp. 162-169.
Stapleton et al,, Measurement of Polybrominated Diphenyl Ethers on Hand Wipes: Estimating Exposure from Hand-to-Mouth Contact, Environ Sci Technol. 2008, 42 (9): 3329-3334.
Staton et al., Dermal nickel exposure associated with coin handling and in various occupational settings: assessment using a newly developed finger immersion method, British Journal of Dermatology, vol. 154, Issue 4, pp. 658-664, Apr. 2006.
Stroo et al., Dermal Bioavailability of Benzo[a ]pyrene on Lampblack: Implications for Risk Assessment, Environmental Toxicology and Chemistry, vol. 24, Issue 6, 2005, pp. 1568-1572.
Theler et al., Clinical Expression of Nickel Contact Dermatitis Primed by Diagnostic Patch Test, Dermatology 2009;219:73-76.
Vaananen et al., Dermal Exposure to Polycyclic Aromatic Hydrocarbons among Road Pavers, Ann. Occup. Hyg., vol. 49, No. 2, (2005), pp. 167-178.

\* cited by examiner

METHODS OF MEASURING METAL POLLUTANTS ON SKIN

FIELD OF THE INVENTION

This application is directed to methods of measuring airborne metals on skin, particularly those that are found in pollution.

BACKGROUND OF THE INVENTION

Skin, especially those portions of the skin not often covered by clothing, is regularly exposed to the environment. So, when the environment to which one is exposed contains air pollution, your skin is also exposed to the air pollution. While we can sense dirt or grime deposited on the skin from air pollution, we cannot tell by looking whether that dirt or grime contains airborne elements, like metals, from the pollution. As such, there is a need to detect and measure airborne metal pollutants on skin.

SUMMARY OF THE INVENTION

A method of measuring airborne metal pollutants on skin, comprising: a) applying to the skin area of interest a tape strip having a peel force sufficient to remove skin cells from the skin when removed from the skin area; b) removing the tape strip; c) placing the tape strip in a clean container; d) digesting a target metal from the tape strip forming a tape strip digestion solution; e) digesting the target metal from a blank tape strip forming a blank tape strip digestion solution in a second clean container in the same manner as the tape strip placed on the skin, wherein the blank tape strip has not been placed on the skin; f) measuring the level of the target metal from the tape strip digestion solution using inductively coupled plasma tandem mass spectrometry; g) measuring the level of the target metal from the blank tape strip digestion solution in the same manner as the tape strip placed of the skin; and h) calculating the level of target metal from the tape strip digestion solution accounting for the level of the target metal from the blank tape strip digestion solution.

A method of measuring an airborne metal on skin, comprising: a) preparing a first skin sample from a subject for measurement of a target metal via inductively coupled plasma tandem mass spectrometry; b) preparing a second skin sample from the subject for measurement of the target metal via inductively coupled plasma tandem mass spectrometry; and c) measuring the target metal in the first and second skin samples with inductively coupled plasma tandem mass spectrometry; wherein the first skin sample is from an area of skin exposed to an airborne metal pollutant and the second skin sample is from an area of skin routinely covered by clothing.

A method of measuring airborne metal pollutants on skin, comprising: a) selecting a tape strip with a peel force sufficient to remove skin cells from the skin when removed; b) applying the tape strip to an area of skin; c) removing the tape strip with a skin sample; d) repeating a, b, and c at least 5 times utilizing a new tape strip each time on the same area of skin; e) placing each tape strip in a separate clean container; f) preparing the skin sample for measurement; g) measuring the level of a target metal in each digested skin sample with inductively coupled plasma tandem mass spectrometry; and h) correcting for any contribution from the tape strip in each sample; wherein the level of target metal in each successive tape strip can show the level of target metal penetration into the skin.

A method of identifying a skin cleanser which can reduce the amount of airborne pollution on skin, comprising: a) identifying a subject with pollution on at least a portion of the skin; b) applying a first tape strip to a skin collection site on the subject; c) removing the first tape strip with a first skin sample from the first skin collection site; d) placing the first tape strip in a container; e) washing a comparable second skin collection site with a skin cleanser; f) allowing the second skin collection site to dry; g) applying a second tape strip to the second skin collection site; h) removing the second tape strip with a second skin sample from the second skin collection site; i) placing the second tape strip in a container; j) digesting the first skin sample to form a first digestion solution and the second skin sample to form a second digestion solution; and k) measuring the level of a target metal from the first digestion solution and second digestion solution using inductively coupled plasma tandem mass spectrometry; wherein a decrease of 10% or more from the first strip to the second strip indicates the ability of the skin cleanser to remove at least a portion of the target metal from the surface of the skin.

DETAILED DESCRIPTION OF THE INVENTION

Figure 1:
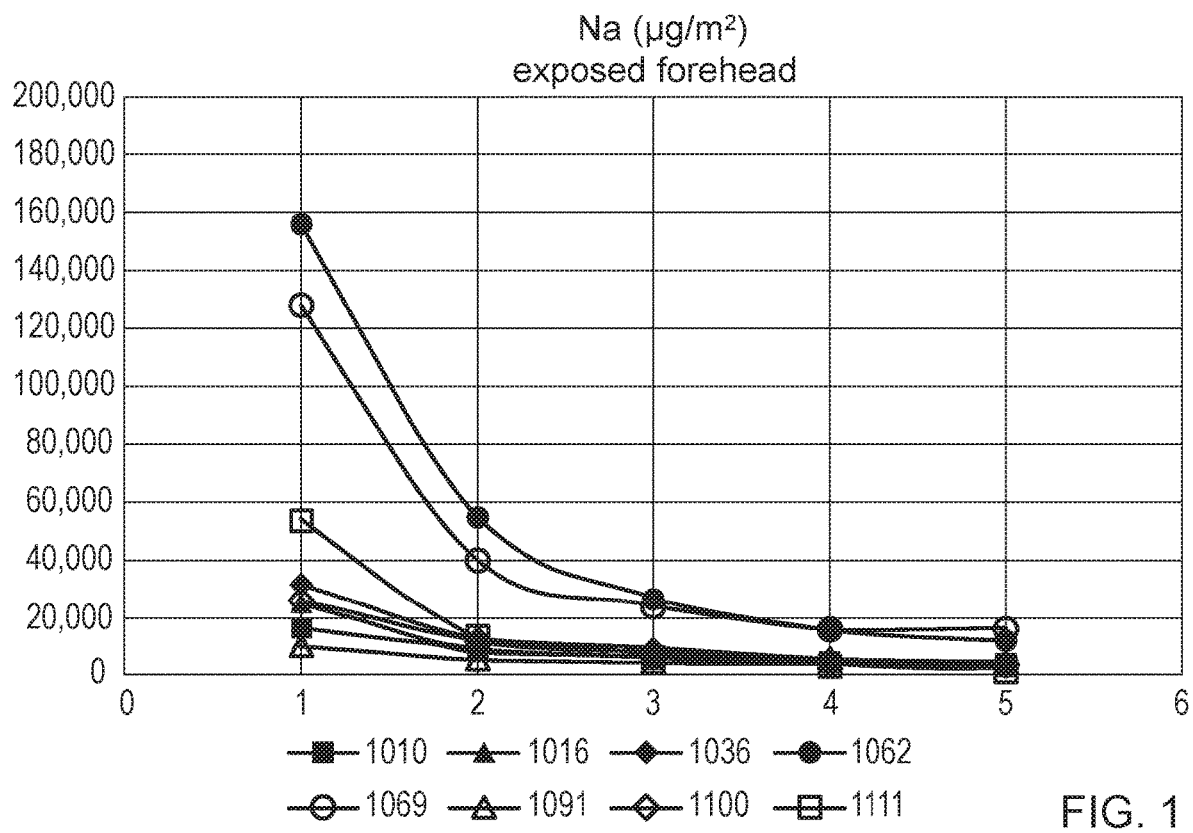
FIG. 1 is a graph of the sodium levels measured on the exposed forehead of subjects.

Air pollution and its impact on those exposed to it are a very real concern, especially to those living or working in high pollution areas. One type of air pollutant that can often be found in these areas is inorganic metal pollutants. These airborne pollutants can deposit onto the skin and have negative impacts on the skin, like contact dermatitis.

Metal, as used herein with respect to metals being measured, refers to those materials which are categorized as a metal in the periodic table and/or described as a metal within a non-metal group on the periodic table (ex. Uranium is categorized as within the actinide series, but is described as a metal within the actinide series). The measurement of trace metals on the skin presents a number of technical challenges due to low exposure and limited airborne pollutant mass on the skin. Sensitivity in the range of picograms is needed for some metals and the measurement needs to be able to stand out from any elemental background created by the collection method. In addition, when looking at such low levels of airborne metal pollutants, care needs to be taken so as to avoid contamination during collection and processing.

Previous attempts to measure materials found on the skin utilized cloths to wipe the skin. While such methods have the advantage of utilizing a larger surface area of skin than some other methods, they have the disadvantage of having inefficient removal of the materials from the skin and generally only remove materials from the surface of the skin. Other methods can include scraping the skin with a scalpel and excising the skin. Both of these methods can be invasive to the subject. In addition, there is also less specificity with these types of collection, meaning it is difficult, if not impossible, to tell where, within the skin layers, the material of interest was predominantly found or the distribution of the target material within the skin layers. The lack of specificity as to where within the skin the metal is found makes it difficult, if not impossible, to distinguish between metal that has come from outside the body and that which has come from the inside of the body, like through ingestion.

Another method of collection of materials from the skin is with the use of an absorbent pad. The pad can be impregnated with a reagent which will help to extract the target material from the skin. The pad is then placed on the skin and left there for a sufficient amount of time to allow for the absorption of the target material into the pad. The disadvantages of this method of collection, similar to above, is that there is a lack of specificity as to where the target materials were within the skin. In addition, if you are looking for more than one target material, you may have to place more than one pad for collection as the reagents needed for collection may be different. Moreover, this method can be time consuming as the pad may need to be in contact with the skin for 15 minutes or even longer.

An additional method of collecting materials from the skin can include the use of adhesive strips, also known as tape strips. These tape strips are generally adhesive on one side. They are placed on the skin, left in place for a minimal amount of time, and then removed from the skin. The benefit from using a tape strip is that the tape strip can remove both skin cells and other materials on the skin due to the adhesiveness of the strip. This allows for a higher amount of extraction efficiency.

A disadvantage of a tape strip is the amount of surface area that can be collected at one time. Due to the operation of the tape strip, it is difficult to collect from a large surface area. This means that the amount of sample taken can be small per strip and, thus, it can need to be combined with a sensitive extraction and measuring method if you are looking for a target material that you are expecting to be in relatively small quantities and/or have a low sensitivity. To compensate for this, tape strips are often used when the test method includes the loading of a material onto the skin. For example, when one is purposefully putting a material onto the skin in moderate quantities and want to measure the amount of material deposited.

Another disadvantage of tape strips is that the collected sample resides in contact with the adhesive. This means generally means the sample has to be extracted/removed from or with the adhesive before it can be measured. Depending on what you are trying to measure, the amount of sample, and whether you are looking for qualitative or quantitative values, this can be arduous.

In addition, the adhesive itself may contain some of the target material based on its formulation or trace contaminants from raw materials. This can impact the results, especially quantitative results for low amounts of the target material. Interestingly, this impact is often ignored in the literature. It is believed, however, this is largely due to the primary use of this collection method where larger amounts of a target material are expected or for qualitative results.

As discussed briefly above, once the skin sample is collected, the skin sample needs to be prepared for measurement and/or measured for the target metal. One method of measuring metals in a sample is through the use of inductively coupled plasma tandem mass spectrometry (ICP-MS/MS). ICP-MS/MS is capable of detecting elements (metals and non-metals) at concentrations as low as one part per quadrillion. While ICP-MS/MS has the sensitivity that is desirable for use with a collection method that produces a small sample size or where the target material is expected to be at a very low level, the sensitivity is limited for those collection methods where there could be interference or background issues, like tape strips.

In addition to providing a small sample size, the tape strips themselves can also provide background issues for the measurement of airborne metals on the skin through contamination of the strips by exposure to the air or from the chemical make-up of the adhesive on the strip or the strip material. In order to utilize this method in combination with a tape strip collection method and provide an accurate result, these potential sources of metals should be accounted for. It has been found that one way to do this, is to treat a blank test strip in the same manner as the test strip and measure the blank test strip for the target metal. For example, if the test strip is digested in an acid, then the blank test strip is digested in the same acid for the same amount of time. Once the digested material (i.e. digestion solution) from both the test strip and the blank test strip are measured, the amount of target metal in the blank test strip can be subtracted from the amount in the test strip to correct for any contribution from the strip. The most accurate way to do this is to treat and measure a blank test strip each time a test strip is measured, however, this could be short cut such that it is measured for a group of strips from a particular lot of strips and the average used for correction of all measurements made using that lot of strips. This could also be done across strip lots or a measurement used on one lot could be reapplied across lots.

Another benefit of the combination of tape strips as the collection method and the ICP-MS/MS as the method of measurement is the ability to measure how the metal pollutant is distributed within the skin layers. For example, multiple test strips can be placed and removed, one after the other, on the same area of skin to get a depth profile. While it is believed that the presence of a target metal within the first few strips is likely from an external pollution source, looking at subsequent tape strips can help to see if there is the potential for contribution from an internal source, like ingestion. When the concentration of a pollutant metal is high in the skin on the first or most exterior tape strip, and decreases in the skin as a function of depth on subsequent tape strips, the exposure is from an external source. Generally, the metal concentration on lower tapes in the skin decay to a relatively steady concentration value, which is a basal level in the skin resulting from steady state exposure to all sources, but which may be attributed to ingestion. When the metal concentration in the skin on interior (deeper) tape strips from an exposed location such as the face is the same as the concentration on interior tape strips from a part of the skin protected by clothing, for example, this is further evidence of exposure from an internal source such as ingestion.

Another benefit of the combination of tape strips and ICP-MS/MS is the ability to assess whether a cleansing composition can at least partially remove pollution from the skin. For example, one can: select a first area of skin, like the forehead, utilize a tape strip to collect and ICP-MS/MS to measure a target metal on that non-treated area; wash a second, different portion of the area of skin, like the other side of the forehead, with a skin cleanser; use a second tape strip to collect and ICP-MS/MS to measure the target metal on the second, treated-portion of the area of skin; and comparing the level of the target metal between the treated and non-treated portions of the area of skin. It is believed a decrease of about 10% or more in the level of target metal in the treated portion as compared to the non-treated portion suggests an ability by the tested skin cleanser to remove at least a portion of the target metal tested.

Moreover, there are benefits to utilizing ICP-MS/MS which can be realized regardless of the collection method. This can include the comparison of exposed skin to unexposed skin on the same subject as further evidence that a target metal collected from the skin of that subject is from a pollution source versus an internal source. Exposed skin is skin that is routinely directly exposed to airborne pollutants, like the face, neck, lower arms, and lower legs, while unexposed skin is generally covered in an outdoor environment like the upper arms, chest, back, buttocks and upper legs. These descriptions are general in nature, however, and each situation should be assessed for the regular clothing habits in both the area and of the individual as these can vary. It is believed that higher levels of a target metal on the exterior layer of skin on an exposed area versus an unexposed area is indicative of air pollution as the major contributor to the target metal on the skin, when the metal is identified as a pollutant.

Tape Strip Collection

A tape strip is adhesive on at least one side and can include any tape strip of any appropriate shape and size. One example of an acceptable tape strip is the D-Squame 3 cm tape strip from CuDerm. The tape strip can contain a backing and an adhesive. The tape strip can have, for example, a surface area of about 1 cm$^2$ to about 12 cm$^2$.

The adhesive needs to be strong enough to remove a target metal from the skin. In order to ensure ample skin is removed from the target surface with a tape strip, the peel force can be measured for a tape by an adaptation of ASTM D3330 Method A, adjusting the method to accommodate tape size and geometry. This method estimates the amount of force needed to peel a tape from a stainless steel plate. Because tape strips are generally round, they can be cut into strips and an additional long tape used to attach the skin tape to the instrument. The instrument peels the tape at the prescribed 180 degree geometry at 10 in/min speed and the steady state force is averaged generally over at least about 5 seconds or more, depending on tape size. The peel force is normalized for the tape width by dividing the steady state force in grams-force, divided by the tape width in cm.

As can be seen below in Table 1, the peel force for different tapes is measured and compared to their mass uptake from the exterior forehead. As the peel force increases kc, the mass uptake reaches a plateau. This is the point at which the peel force of the tape strip is equal or greater than the cohesiveness of the stratum corneum and the maximum load of skin sample is reached. Values shown are mass removal from the top most layer of skin. This is observed to happen between Adhesive Tapes 6 and 7. Thus, the minimum peel force value for a tape is around 10 or 20 or 25 or 30 or 40 or 50 g/cm.

TABLE 1

| | Peel Force (g/cm) | Mass Uptake (exterior forehead tape mass increase/ mg/cm$^2$) | Mass uptake calculated for standard 2.2 cm D-Squame/mg | Acceptable or Unacceptable for the standard 2.2 cm D-Squame tape size |
|---|---|---|---|---|
| Adhesive Tape 1 | 166 | 0.20 mg/cm$^2$ | 0.760 | Acceptable |
| Adhesive Tape 2 | 114 | 0.15 mg/cm$^2$ | 0.570 | Acceptable |
| Adhesive Tape 3 | 160 | 0.28 mg/cm$^2$ | 1.064 | Acceptable |
| Adhesive Tape 4 | 119 | 0.13 mg/cm$^2$ | 0.494 | Acceptable |
| Adhesive Tape 5 | 82 | 0.33 mg/cm$^2$ | 1.254 | Acceptable |
| Adhesive Tape 6 | 71 | 0.36 mg/cm$^2$ | 1.368 | Acceptable |
| Adhesive Tape 7 | 4 | 0.03 mg/cm$^2$ | 0.114 | Unacceptable |

However, it is important to understand how much sample (i.e. skin plus other materials removed from the skin on the tape) can be removed from the skin per strip. Thus, a strip with a low surface area, for example around 1.1 cm$^2$ area, and an adequate peel force, for example around 166 g/cm, may remove about 0.22 mg of skin sample from the skin surface. It is believed that a target of about 0.20 mg or more per tape strip will allow for an adequate amount of sample for measurement for most, if not all, of the target metals. It should be noted, however, where the target metal has a higher sensitivity, a lower amount of skin sample per tape strip could be acceptable. With a low amount of sample, less target metals can be detected. See, for example, Table 2 below.

In Table 2, the amount of sample collected from the tape is labeled SC (stratum corneum) protein. When comparing tape strips from the same collection area, like the buttock, cesium is not detected on either Tape 5 or Tape 3 which had sample masses of 13.0 μg/cm$^2$ and 14.1 μg/cm$^2$, respectively. Cesium was, however, detected on Tape 1, which had a sample mass of 34.4 μg/cm$^2$. Moreover, if you look at cesium on the forehead collection area, it is noted that it can be detected on a tape with a level as low as 8.5 μg/cm$^2$, which is lower than the level needed for detection on the buttock tape. It is believed, however, this is due to a difference in concentration between the two areas. As noted below, a higher concentration of a target metal can allow for a tape strip with a smaller surface area or be detected in a smaller sample size.

TABLE 2

| site | Tape # | SC protein (μg/cm$^2$) | Na (μg/TS) | Mg (μg/TS) | K (μg/TS) | Ca (μg/TS) | V (ng/TS) | Cr (ng/TS) | Mn (ng/TS) | Fe (μg/TS) |
|---|---|---|---|---|---|---|---|---|---|---|
| forehead | 5 | 6.1 | 46,474 | 1,440 | 43,793 | 13,204 | 1,970 | 15,949 | ND | 527 |
| forehead | 3 | 8.5 | 317,082 | 2,295 | 80,843 | 19,548 | 502 | 59,598 | 19,183 | 3,221 |
| forehead | 1 | 15.8 | 341,119 | 6,083 | 167,908 | 32,896 | 7,818 | 48,321 | 100,896 | 8,420 |

TABLE 2-continued

| | | | | | | | | | | |
|---|---|---|---|---|---|---|---|---|---|---|
| buttock | 5 | 13.0 | 22,962 | 865 | 30,025 | 6,327 | 890 | 10,389 | ND | 258 |
| buttock | 3 | 14.1 | 204,068 | 1,426 | 57,108 | 4,995 | 1,083 | 412 | 3,786 | 300 |
| buttock | 1 | 34.4 | 227,612 | 3,739 | 323,888 | 18,304 | 3,496 | 11,181 | 35,199 | 2,195 |

| Ni (ng/TS) | Cu (ng/TS) | Zn (ng/TS) | As (ng/TS) | Rb (ng/TS) | Sr (ng/TS) | Cd (ng/TS) | Cs (ng/TS) | La (ng/TS) | Pb (ng/TS) | U (ng/TS) |
|---|---|---|---|---|---|---|---|---|---|---|
| 19,512 | 49,583 | 399,114 | ND | 46,394 | 19,274 | 21,973 | ND | 78 | ND | 339 |
| 22,544 | 182,345 | 1,470,415 | ND | 86,500 | 56,366 | 17,210 | 131 | 398 | 5,831 | 138 |
| 1,193,135 | 1,419,427 | 880,055 | 10,411 | 133,835 | 83,432 | 1,695 | 680 | 2,388 | 69,380 | 1,157 |
| ND | 11,346 | 71,394 | 1,215 | 23,789 | 80,982 | 237 | ND | 11 | 22,940 | 241 |
| ND | 11,287 | 25,819 | 6,558 | 47,533 | 28,467 | 118 | ND | 2,464 | 6,170 | 89 |
| 10,590 | 33,443 | 116,653 | 19,149 | 273,757 | 37,772 | 284 | 1,364 | 983 | 9,684 | 408 |

It is believed that a target of about 0.20 mg or more per tape strip will allow for an adequate amount of sample for measurement for most, if not all, of the target metals. It should be noted, however, where the target metal has a higher sensitivity, a lower amount of skin sample per tape strip could be acceptable.

While the amount of skin sample that will be picked up by a given tape strip can be estimated based on the peel force and surface area, as discussed above, the actual amount of sample on a tape strip after removal can be measured. To do this, an individual tape strip is weighed just before application to the skin and then immediately following removal from the skin. Having this information allows for results to be translated into the amount of pollution deposited per area to pollution per mass of skin removed gravimetrically. In addition, it allows for results between tapes to be normalized as one tape may have more pollutant simply because more mass of skin came off on that tape, if the pollutant is embedded in the skin. However, gravimetric measurements are time consuming and can be inaccurate at low mass uptake levels.

Another way to measure the amount of skin collected on a tape strip is to measure the optical clarity of the strip both before and after collection. Optical clarity can be measured as percent absorption @ 850 nm using a Squame Scan instrument from CuDerm or similar. This measurement can then be translated into soluble protein content using a simple transfer function.

A tape strip can be placed on an area of skin. The tape strip is in contact with the skin long enough to adhere to the skin layer. The tape strip should be applied with sufficient pressure to allow it to adhere to the skin. This can be done manually by applying pressure with the fingers or hand or can be done mechanically if a more controlled pressure at application is desired. An example of mechanical application can include the use of a roller and/or a pressure device. A target pressure could be, for example, about 225 g/cm$^2$ using the 7/8 inch diameter spring loaded device for this purpose from CuDerm. The pressure may be applied for about 5 seconds or more. Both the test population and the area of skin to be tested can be selected based on the intended use of the data. For example, if the purpose of the sampling is to understand deposition of a target metal from airborne pollution, the test population can be selected based on whether such subject lives or works in an environment having an airborne Total Suspended Particles (TSP) regularly higher than 60 µg/m$^3$ (polluted environment). In addition, to study the greatest potential deposition of airborne pollution on skin, one can choose those areas of skin which are routinely not covered, like the face, neck lower arms, and lower legs, and also areas where particles may impact and adhere to the skin due to their relative velocity, such as the face, for example when walking forward or bicycling. In addition, to assess the difference between exposed and unexposed skin, one can choose to also sample from an area of the body generally covered in an outdoor environment like the upper arms, chest, back, buttocks and upper legs. These designations, of course, will depend on the region, season, and generally accepted attire in the area.

Once appropriately applied, the tape strip will be removed. As the tape strip is removed, a skin sample is removed with it. The tape strip can be removed with fingers, however, care should be taken not to contaminate the sample. This can be accomplished using gloves. The gloves can also be rinsed and dried prior to removal to further help reduce contamination. The strips can also be removed with a tool, like forceps or tweezers. The tool should also be clean and free of rust or it could contaminate the sample. Having a Teflon coating on the tool can also be helpful.

Once removed, the skin sample can then be tested for a target metal. The tape strip can be placed into a storage container or immediately prepared for testing. Where more than one test strip is taken during a test, the tape strips can be placed in separate containers or aggregated into one container as the data being collected will allow.

Tape stripping also allows for the collection of multiple tapes from the same site. This allows for the evaluation of the level of penetration of a target metal into the skin. It can also help determine whether a target metal is from an internal source, like ingestion, versus an external source, like pollution. Tape strips can be used until the glistening layer is reached. Past this point, the skin can be damaged and it can become more painful for the subject. The number of tape strips that can be applied and removed on one area, for example, are from about 1 to about 20, or about 5 or about 10. Tape strips from different areas can also be taken and compared for various purposes as discussed above.

Inductively Coupled Plasma Tandem Mass Spectrometry

To prepare a tape strip for measurement of the target metal according to ICP-MS/MS, the target metal is digested or dissolved from the tape strip to form a digestion solution. Digestion can include the digestion of the metal from the tape strip, the digestion of the skin sample and the target metal from the tape strip, the digestion of the skin sample and the adhesive and the target metal from the tape strip, the digestion of the entire tape strip, or some combination thereof. As discussed in further detail below, any correction for the tape strip takes into account which of the materials (metal, adhesive, tape strip, or all) is digested as the blank tape strip is treated in the same manner as the testing tape strip.

To digest the tape strip (or a portion thereof as discussed above), an appropriate reagent is chosen. This reagent can be an acid or include an acid, for example, nitric acid, hydrofluoric acid, or a combination thereof. The digestion can also include the use of heat. Heat can be introduced to the sample, for example, by the use of a hot block or microwave digestion system. The tape strip is placed into an appropriate container for digestion, like a plastic centrifuge tube. The tape strip can be placed in the container as is. To avoid the tape strip sticking to the side of the container, the tape strip can also be folded in half with the adhesive portion of the adhesive strip on the inside. The tape strip should remain in the reagent until the sample is digested. The sample is digested when the adhesive material has been removed from the plastic backing of the tape strip and the solution is clear except for the un-digested tape strip backing or where the entire tape strip is digested, the sample is digested if the entire tape strip is dissolved and the solution is clear. Digesting a sample could include, for example, adding 50% Nitric Acid (v/v from a 70% w/w solution) and 1.25% HF (v/v from a 50% w/w solution) to a container containing the tape strip with skin sample and using a hot-block set at 105° C., where the samples were loosely capped and kept on the heat for 120 min. It is believed the temperature of the digestion mixture on a hot plate of 105° C. is between 86 and 97° C.

When measuring the digestion solution in accordance with the ICP-MS/MS Method, any contribution of a target metal to the sample from the digested portion of the tape strip can be accounted for in order to give an accurate quantity of target metal from the sample. To do this, a blank tape strip is treated in the same manner as the test tape strip (i.e. stored and digested in the same manner as the test tape strip). Then, any amount of target metal found in the blank test strip can be subtracted from the value of the target metal in the test tape strip to correct for any contribution of the blank test strip, as discussed in more detail above.

The digested sample can be measured for a target metal. A target metal can include, for example, lead, sodium, magnesium, potassium, calcium, vanadium, chromium, manganese, iron, nickel, copper, zinc, arsenic, rubidium, strontium, cadmium, cesium, lanthanum, uranium, or a combination thereof. Target metals are analyzed in the digested solution by aspirating/pumping the solution into the ICP-MS/MS instrument. Analysis is based on well-established ICP-MS/MS methodologies. Briefly, the metals in the solution are ionized by the argon plasma and the charged atoms are separated based on their mass/charge ratio in the first quadrupole (QS), the middle reaction/collision chamber can be employed to remove or react isobaric interferences from the mass of interest (depending on element) and the resulting ion beam is further separated in the second quadrupole (Q2). Ions are detected and the signal is proportional to the amount metal in the solution. An external calibration curve of known concentration of each element is also analyzed and used to generate a calibration curve. Quality control samples are also analyzed to ensure accurate results.

The level of target metal found in the digested sample can be corrected for background contributions from the tape strip, as discussed above. In addition, a target metal can come from a variety of airborne sources (dust, dander, other biological material) that are not pollution and make its way onto the skin to be detected by this technique. In order to determine whether the target metal found on the skin came from pollution or a non-pollution source, a geological record can be consulted. A geological record is generally a reference giving the levels of metals found in the soil in the region of interest. One example of a geological record is Taylor S R, Abundance of chemical elements in the continental crust: a new table, Geochim et Cosmochim Acta 28, 1273-1285 (1964). The level of target metal in the region from the geological source is then compared to the level found on the skin. Where the level of target metal found on the skin, after any background level is accounted for, is at least 5 times greater than the level in the geological record, then the level on the skin is considered anthropogenically enriched (i.e. the level on the skin can be attributed to pollution).

Results are reported based on the levels found on the sample with any adjustment as noted above for the tape strip. For sodium, magnesium, potassium, calcium, and iron, results can be reported in μg per tape strip. For vanadium, chromium, manganese, nickel, copper, zinc, arsenic, rubidium, strontium, cadmium, cesium, lanthanum, uranium, and lead can be reported in ng per tape strip.

EXAMPLES

Some results of target metal measurements are included below. Results are presented in a pair of graphs which represent the exposed forehead skin and the unexposed buttock skin of outdoor workers in the inner city area of Beijing, China. Individuals like these can be sampled and measured in accordance with the Tape Strip Method and ICP-MS/MS method listed below, where the steps are adjusted as needed based on the data collected. For example, there was no treatment leg here, so there was no collection and measurement after treatment.

A) Sodium (Na)

Figure 2:
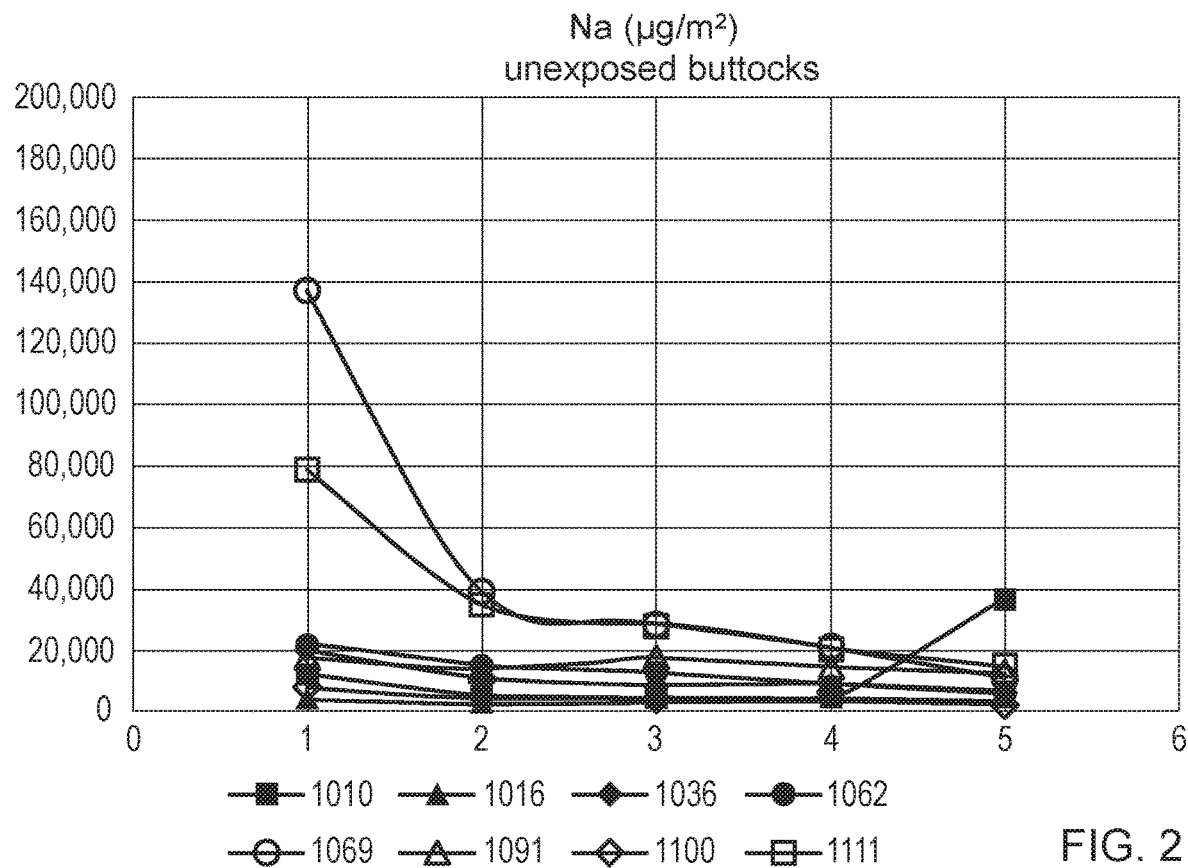
FIG. 2 is a graph of the sodium levels measured on unexposed buttock skin of the same subjects.

FIG. 1 is a graph of the sodium levels measured on the exposed foreheads of subjects after a day at work in a polluted environment. FIG. 2 is a graph of the sodium levels measured on unexposed buttock skin of the same subjects. Each graph shows results for 5 successive tape strips for each subject showing the skin exterior surface (tape 1) to the lowest tape measured (tape 5).

Sodium is elevated in human sweat. Its high levels in this study indicate exertion. When we measured employees in an office environment, we found a much lower level, about 2,000 μg/m$^2$ of Na on the forehead. Levels were comparable on both body sites. Individual differences may be explained by differences in sweat rate, although subjects were not prohibited from wiping their skin during the study. Without other data, it would be difficult to differentiate sodium delivered to the skin by sweating compared to environmental sources such as airborne TSP.

B) Zinc (Zn)

Figure 3:
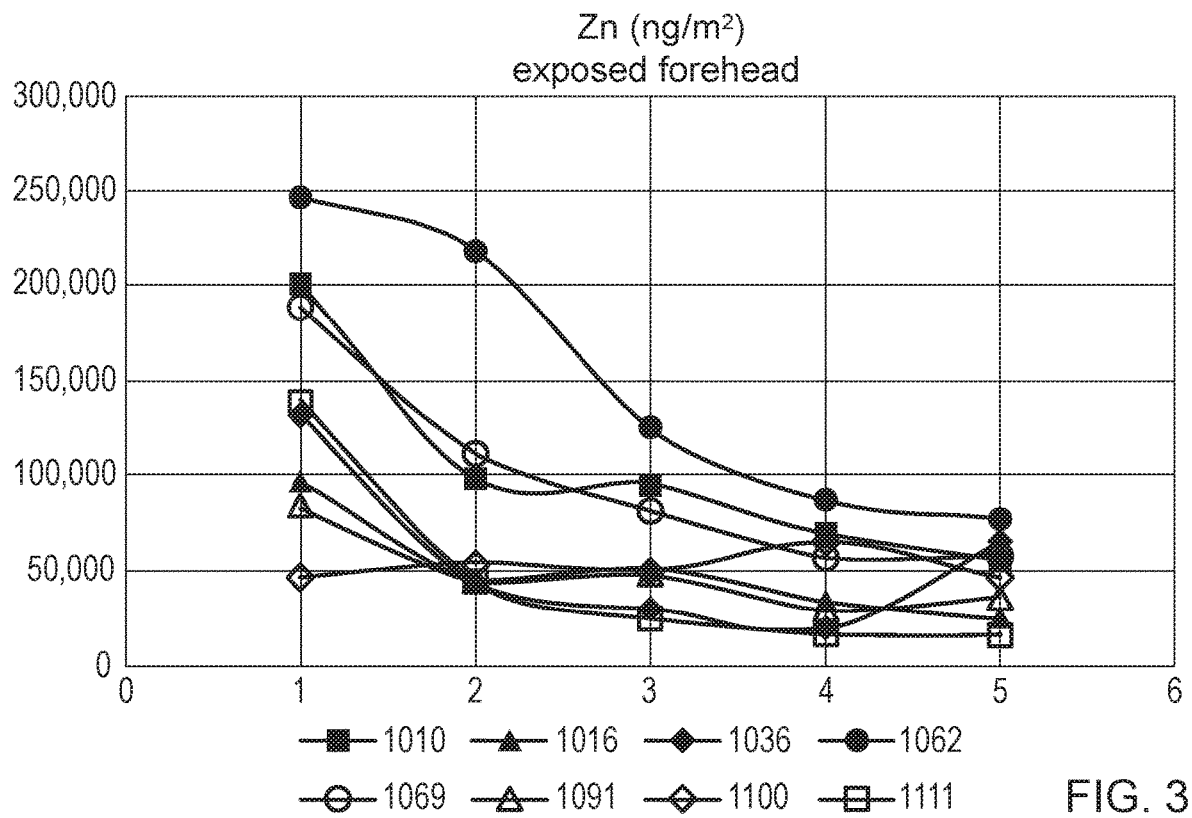
FIG. 3 is a graph of the zinc levels measured on the exposed forehead of subjects.
Figure 4:
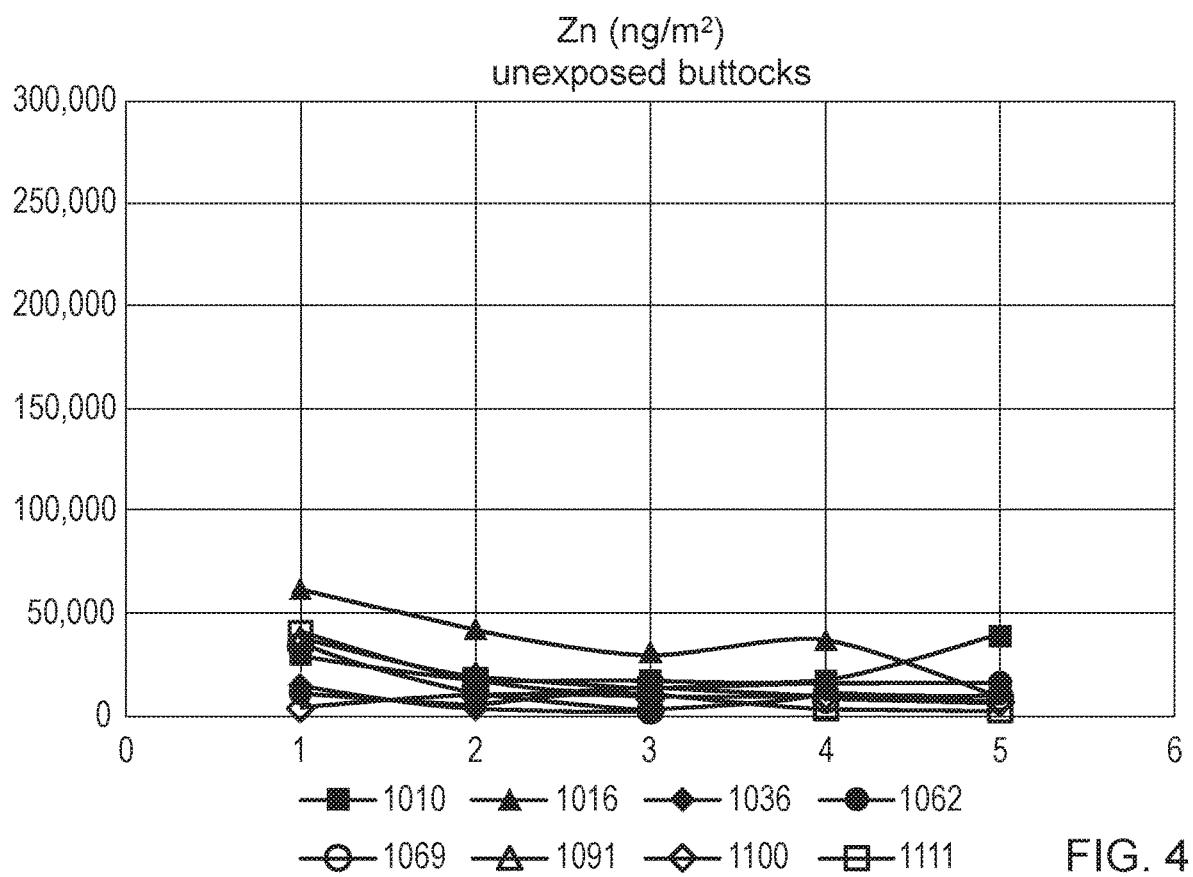
FIG. 4 is a graph of the zinc levels measured on unexposed buttock skin of the same subjects.

FIG. 3 is a graph of the zinc levels measured on the exposed forehead of subjects. FIG. 4 is a graph of the zinc levels measured on the unexposed buttock skin of the same subjects. Each graph shows results for 5 tape strips for each subject showing the skin exterior surface (tape 1) to the lowest tape measured (tape 5).

Increased levels of zinc are evident primarily on exposed forehead tapes, about 4-fold more than tapes from unexposed, buttock skin. This indicates the presence of airborne pollution containing zinc had been deposited on the skin. The presence of zinc in airborne pollution in this area is common due to its ubiquitous use as a refined metal, so its abundance may make it a target pollutant for cleaning.

C) Cadmium (Cd) and Lead (Pb)

Figure 5:
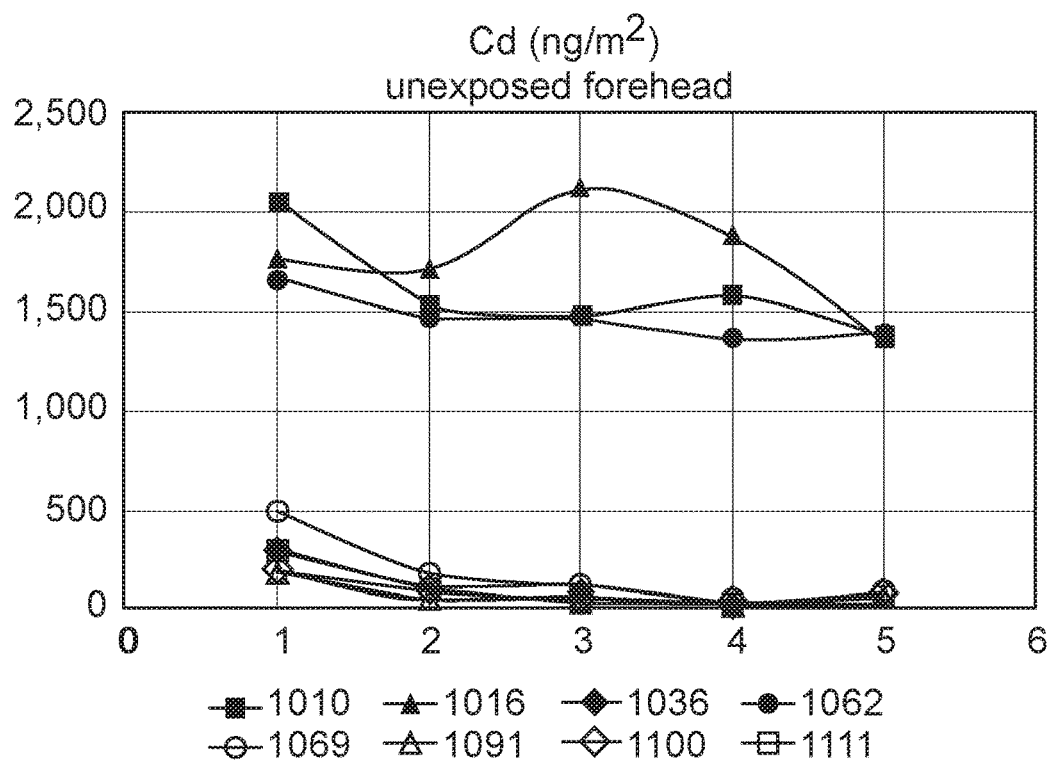
FIG. 5 is a graph of the cadmium levels measured on the exposed forehead of subjects.
Figure 6:
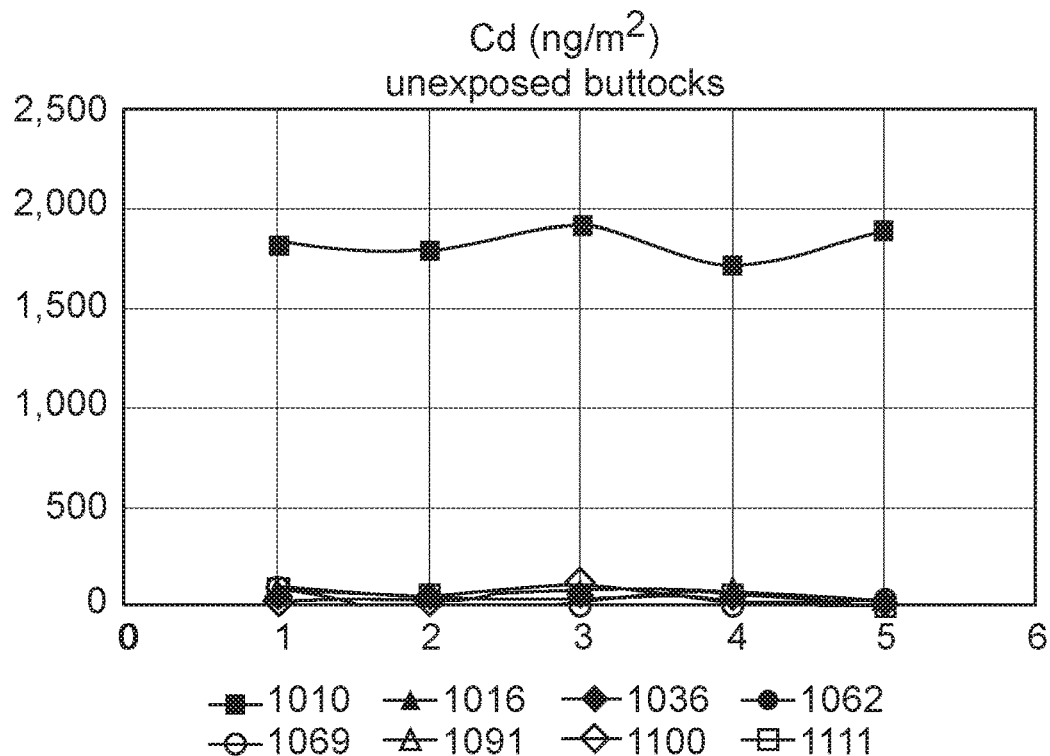
FIG. 6 is a graph of the cadmium levels measured on unexposed buttock skin of the same subjects.
Figure 7:
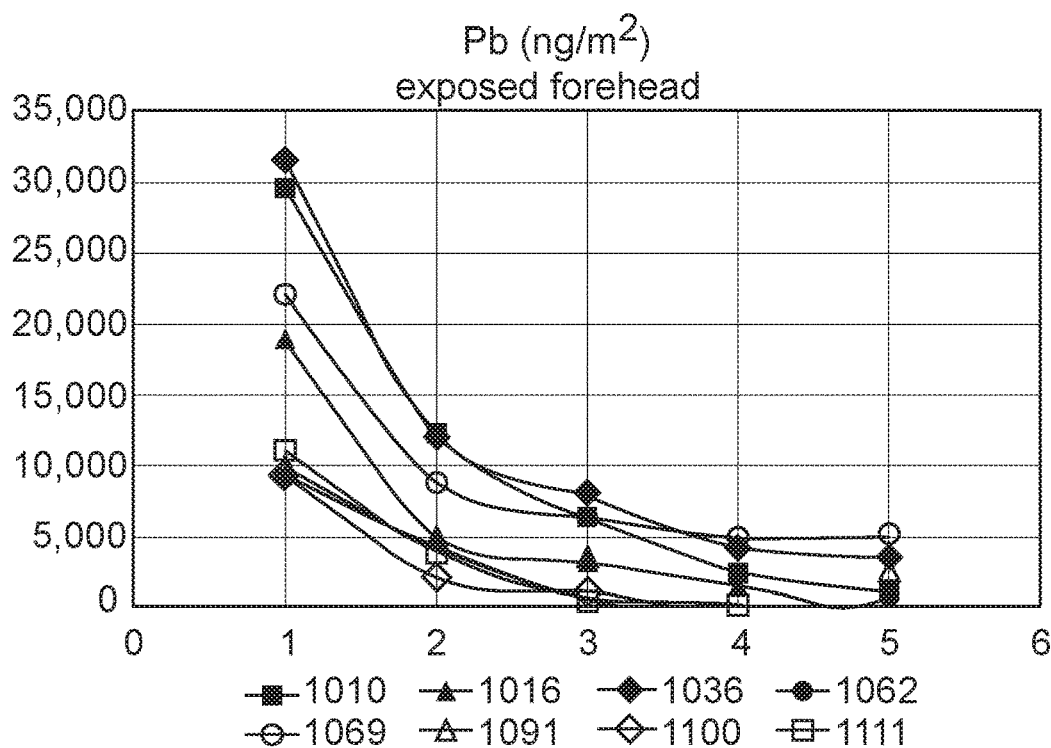
FIG. 7 is a graph of the lead levels measured on the exposed forehead of subjects.
Figure 8:
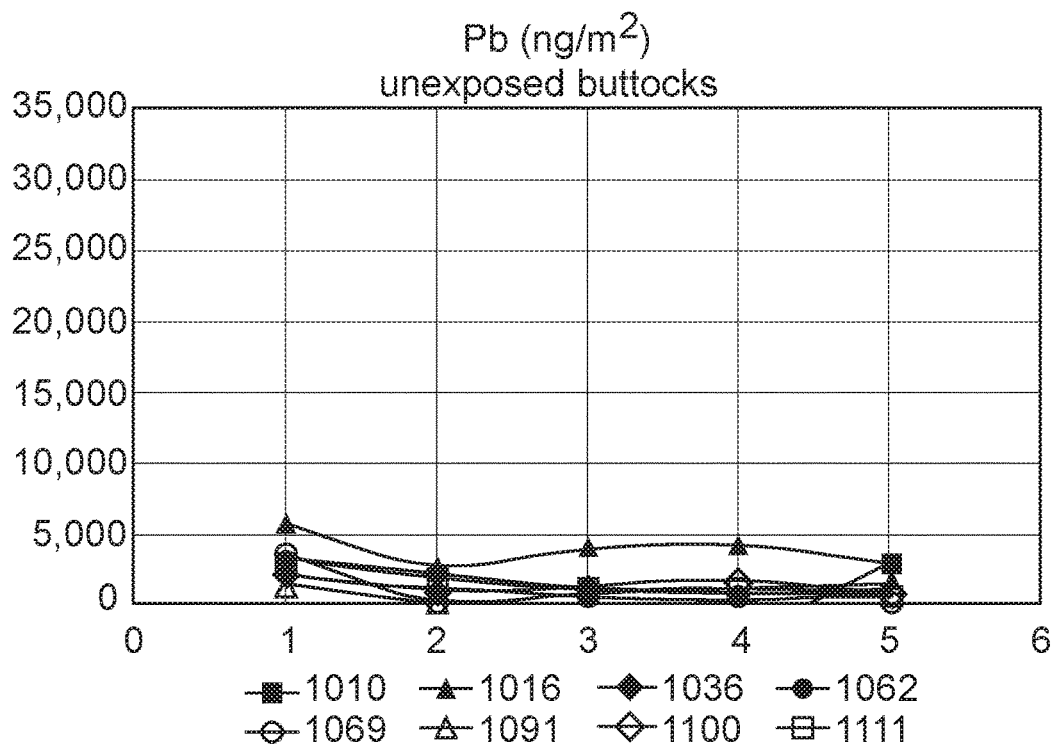
FIG. 8 is a graph of the lead levels measured on unexposed buttock skin of the same subjects.

FIG. 5 is a graph of the cadmium levels measured on the exposed forehead of subjects. FIG. 6 is a graph of the cadmium levels measured on the unexposed buttock skin of the same subjects. FIG. 7 is a graph of the lead levels measured on the exposed forehead of subjects. FIG. 8 is a graph of the lead levels measured on the unexposed buttock skin of the same subjects. Each graph shows results for 5 tape strips for each subject showing the skin exterior surface (tape 1) to the lowest tape measured (tape 5).

Cadmium and lead are toxic heavy metals and can be emitted into the air from multiple pollution sources. Coal burned in China is reported to be high in both metals and, although leaded gasoline has not been used in China since 1997, literature suggests urban road dust residues may retain high levels of lead even today. Three subjects show evidence of very high exposure to cadmium. All eight subjects had higher lead levels on exposed skin tapes 1 and 2. This indicates these materials are likely attributable to pollution and could be important targets for skin cleansing for air pollution removal.

Test Methods

Tape Strip Method

Select subjects based on criteria. Obtain tapes with a backing and an adhesive having a peel force greater than 10 g/cm width as measured by the Adapted ASTM D3330 Method A, adjusting the method to accommodate tape size and geometry, as discussed above. Remove a tape from the backing, as required. Press a tape to an exposed skin surface. Apply pressure from a standard device, like a roller for 5 seconds, as desired. Mark the skin near the edge of the tape for accurate application of additional strips to the same area. Remove the tape using clean forceps or tweezers.

Measure the optical transparency of a tape with its skin sample using a zeroed, calibrated instrument such as a Squame Scan®. Store the tape with a suitable label. Repeat the application and removal steps at the same marked site to obtain a second tape. Repeat the procedure to obtain up to 20 skin tapes, or until reaching the glistening layer. Repeat steps as needed for unexposed skin. Repeat steps as needed for treated skin. Remove tapes from storage and optionally, remeasure optical transparency of tapes using calibrated instrument such as a Squame Scan®. Measure target metal (s) on tapes using the ICP-MS/MS Method. Identify target metal(s). Compare metals from exterior tape(s) and interior tape(s), and exposed and unexposed.

ICP-MS/MS Method

This procedure provides a method for the determination and measurement of a target metal (for example, Na, Mg, K, Ca, V, Cr, Mn, Fe, Ni, Cu, Zn, As, Rb, Sr, Cd, Cs, La, Pb and U) on a skin sample, like tape strip samples. While this method is specific to tape strips, it can be adjusted to account for other types of skin sample collection methods. Tape strips are used to sample surfaces, most commonly skin. The most common tape strip used with this method is a D-Squame 3 cm (exact specification 3.016 cm in diameter) stripping disc. Depending on the element, this procedure covers a range between 0.5 ppt (U) and 100 ppm (Na) in solution, which corresponds to 0.005 ng and 1000 µg on a tape strip, respectively. Lower and upper limits of Quantitation (LLOQ and ULOQ) are provided in the table below (assuming standard dilution factor). The ULOQ can be increased with further dilution of the sample as needed.

| | Element | | | | | | | | | |
|---|---|---|---|---|---|---|---|---|---|---|
| | Na | Mg | K | Ca | V | Cr | Mn | Fe | Ni | Cu |
| | | | | | Unit/Tape Strip | | | | | |
| | µg | µg | µg | µg | ng | ng | ng | µg | ng | ng |
| LLOQ | 1 | 0.05 | 0.2 | 0.05 | 0.05 | 2 | 0.25 | 0.05 | 2 | 1 |
| ULOQ | 1000 | 20 | 200 | 20 | 20 | 200 | 100 | 20 | 400 | 400 |

| | Element | | | | | | | | |
|---|---|---|---|---|---|---|---|---|---|
| | Zn | As | Rb | Sr | Cd | Cs | La | Pb | U |
| | | | | | Unit/Tape Strip | | | | |
| | ng | ng | ng | ng | ng | ng | ng | ng | ng |
| LLOQ | 2.5 | 0.4 | 0.2 | 0.4 | 0.05 | 0.02 | 0.0125 | 0.4 | 0.005 |
| ULOQ | 1000 | 400 | 200 | 400 | 20 | 20 | 5 | 400 | 2 |

In this procedure the entire tape strip with picked-up material in a container is placed on a hot block with a mixture of nitric and hydrofluoric acids. After heating on a 105° C. preheated hot block for ~120 min, the solution is diluted with addition of internal standard (like Ga, Tl or Rh—selected based on what is expected not to be in the sample) and analyzed by inductively coupled plasma tandem mass spectrometry (ICP-MS/MS), as discussed in more detail below. A number of blank tape strips is treated in parallel to the actual samples and results are reported for background assessment purposes. Results for Na, Mg, K, Ca and Fe are reported in µg per tape strip, and for V, Cr, Mn, Ni, Cu, Zn, As, Rb, Sr, Cd, Cs, La, Pb and U—in ng per tape strip.

Standard Substances, Apparatus and Special Materials Used in ICP-MS/MS Method

| APPARATUS | SUGGESTED TYPE OR SOURCE (Equivalent Items May be Used) |
|---|---|
| ICP-MS/MS | 8800, Agilent, equipped with ISIS 2 in discrete sample introduction mode |
| Hot block digestion system | Accommodating 15 mL tubes, 108 positions, SCP Science, DigiPrep |

-continued

| APPARATUS | SUGGESTED TYPE OR SOURCE (Equivalent Items May be Used) |
|---|---|
| Calibrated automatic pipettes | 20 µL, 100 µL, 1 mL, and 5 mL, Eppendorf |
| Graduated conical centrifuge tubes | 50 mL and 15 mL, polypropylene (PP), Metal Free, VWR |
| Plastic bottles | Various sizes (250 mL-4 L), polyethylene (PE), VWR |
| Disposable plastic cups | Various sizes (5-100 mL), polystyrene (PS) or PP, VWR |
| Disposable PP spatulas | 21 cm, VWR |
| Analytical balance | Capable to 0.01 g, Mettler Toledo |
| Disposable transfer pipettes | General purpose, PE, VWR |

REAGENTS AND SOLUTIONS (Equivalent Items May Be Used)

Water, deionized (DI), ≥18 MΩ [CAS 7732-18-5]
Nitric acid ($HNO_3$), ultra-high purity/trace metal grade (e.g., BDH, Aristar Ultra) [CAS 7697-37-2]
Hydrofluoric Acid (HF), ultra-high purity/trace metal grade (e.g., BDH, Aristar Ultra) [CAS 7664-39-3]
Nitric Acid, high purity (e.g., BDH, Aristar Plus)
Triton X-100 surfactant, high purity (e.g., EMD Millipore, OmniPur) [CAS 9002-93-1]

STANDARD SOLUTIONS
Custom Standard "PG-28" (Source 1) and Custom Standard "PG-28QC" (Source 2), certified multi-element standard (Inorganic Ventures) was created with metals at the following concentrations:

| | |
|---|---|
| 1000 µg/mL Na | 0.2 µg/mL Cr, Rb |
| 200 µg/mL K | 0.1 µg/mL Mn |
| 20 µg/mL Ca, Fe, Mg | 20 µg/L Cd, Cs, V |
| 1 µg/mL Zn | 5 µg/L La |
| 0.4 µg/mL As, Cu, Pb, Ni, Sr | 2 µg/L U |
| 1 µg/mL Ga | 0.5 µg/mL Tl, Rh |

Certified single elemental standards can be used as a substitute and different concentrations of standards can be used as long as the appropriate adjustments are made when making the calibration curve standards and quality controls (QCs). At least two sources of standard stock solutions should be used for preparation of the calibration and method QC samples. This practice minimizes any errors from a contaminated or adulterated stock solution. The same internal standard stock (same certified concentration) should be used to prepare all solutions in a batch.

The level of metals being analyzed in this method is often very low. Therefore precautionary steps can be taken in order to ensure that metals are not coming from reagents and containers during processing. All containers (graduated cylinders, bottles, cups, conical tubes, etc.) should be rinsed with dilute acid (e.g. up to 50% nitric acid) and then rinsed with deionized (DI) water. Pipet tips should be rinsed with dilute acid and DI water before use.

ICP-MS/MS Rinse 1 is a solution of 20% $HNO_3$, 0.5% HF, and 0.02% Triton X-100.
ICP-MS/MS Rinse 2 is a solution of 50% $HNO_3$.
Rinse 3 is a solution of 2% $HNO_3$ and 0.5% HF.
Autosampler Rinse Station Solution is 2% $HNO_3$.

Standards Preparation

One of two different sources of stock standards will be used to prepare calibration standards and the continuing calibration verification (CCV) quality control (QC) check standard. The CCV is used for periodic checks of the calibration curve stability throughout the analysis on the ICP-MS/MS. A stock standard from the other source will be used to prepare initial verification calibration (ICV) QC check standard to be analyzed once immediately after calibration.

Calibration and QC Check are prepared to match the acid combination used in the samples, this ensures a similar acid matrix (20% $HNO_3$, 0.5% HF) between standards and samples which is good practice for ICP-MS analysis. Internal standard containing Rh, Tl, Ga needs to be added to all standards and samples at the same concentration in test solution or the internal standard can be introduced into the ICP-MS/MS using a t-connection in order to monitor and correct for plasma variations. An example of calibration curve concentrations for each element is provided in the table below. The Standard aliquot volume is based on preparing 50 mL of each standard.

| Solution ID | Standard Aliquot (mL) PG-28 | Standard Aliquot (mL) PG-28QC | ppm Na | ppm K | ppm Ca Fe Mg | ppm Zn | ppb Ni | ppb Cu | ppb As Pb Sr | ppb Cr | ppb Rb | ppb Mn | ppb Cd V | ppb Cs | ppb La | ppb U |
|---|---|---|---|---|---|---|---|---|---|---|---|---|---|---|---|---|
| Calibration Blank/QC Blank Check | 0 | 0 | 0 | 0 | 0 | 0 | 0 | 0 | 0 | 0 | 0 | 0 | 0 | 0 | 0 | 0 |
| Cal Standard 1 | 0.005 | 0 | 0.1 | 0.02 | | | | | 0.04 | | 0.02 | | 0.002 | | | |
| Cal Standard 2 | 0.0125 | 0 | 0.25 | 0.05 | 0.005 | 0.25 | | 0.1 | 0.1 | | 0.05 | 0.025 | 0.005 | 0.005 | 0.00125 | 0.0005 |
| Cal Standard 3 | 0.025 | 0 | 0.5 | 0.1 | 0.01 | 0.5 | 0.2 | 0.2 | 0.2 | | 0.1 | 0.05 | 0.01 | 0.01 | 0.0025 | 0.001 |
| Cal Standard 4 | 0.05 | 0 | 1 | 0.2 | 0.02 | 1 | 0.4 | 0.4 | 0.4 | 0.2 | 0.2 | 0.1 | 0.02 | 0.02 | 0.005 | 0.002 |
| Cal Standard 5 | 0.1 | 0 | 2 | 0.4 | 0.04 | 2 | 0.8 | 0.8 | 0.8 | 0.4 | 0.4 | 0.2 | 0.04 | 0.040 | 0.01 | 0.004 |
| Cal Standard 6/ CCV QC Check | 0.5 | 0 | 10 | 2 | 0.2 | 10 | 4 | 4 | 4 | 2 | 2 | 1 | 0.2 | 0.2 | 0.05 | 0.020 |
| Cal Standard 7 | 2.5 | 0 | 50 | 10 | 1 | 50 | 20 | 20 | 20 | 10 | 10 | 5 | 1 | 1 | 0.25 | 0.1 |
| Cal Standard 8 | 5 | 0 | 100 | 20 | 2 | 100 | 40 | 40 | 40 | 20 | 20 | 10 | 2 | 2 | 0.5 | 0.2 |
| Second Source ICV QC Check | 0 | 0.5 | 10 | 2 | 0.2 | 10 | 4 | 4 | 4 | 2 | 2 | 1 | 0.2 | 0.2 | 0.05 | 0.02 |

QC samples are used to monitor metal level during processing to ensure no contamination occurs (method blank), to monitor tape strip blank level (see above description of importance of Tape Strip Blanks) and to spike a known amount of metals on blank tape strips to ensure that no metals are lost during processing and that accurate values can be archived in sample matrix (Matrix QCs). The number of blanks, blank tape strips, and QC spikes depends on the number of samples analyzed (generally 1 method blank, 2 tape strip blanks and two matrix QCs for every 40 samples). Examples of Matrix QC levels low (LQC), mid (MQC) and high (HQC) are shown in the table below but can vary. These QC check samples are treated like normal samples except for spiking standard onto the tape strip in the case of the matrix QCs and no tape strip is added to the method blank.

If provided, each batch should include one Tape Strip Field Blank (TSFB), which counts toward the number of actual samples. Difference between Tape Strip Blank (TSB) and TSFB is that TSB is an untouched tape strip, as supplied by the manufacturer, and TSFB is a tape strip that was processed and handled the same way as an actual sample but not exposed to skin.

| QC ID | PG-28 Aliquot (mL) | µg Na | µg K | µg Ca, Fe, Mg | ng Zn | ng As, Cu, Pb, Ni, Sr | ng Cr, Rb | ng Mn | ng Cd, Cs, V | ng La | ng U |
|---|---|---|---|---|---|---|---|---|---|---|---|
| | | | | Added amount of analyte per tape strip | | | | | | | |
| Matrix LQC | 0.005 | 5 | 1 | 0.1 | 5 | 2 | 1 | 0.5 | 0.1 | 0.025 | 0.01 |
| Matrix MQC | 0.05 | 50 | 10 | 1 | 50 | 20 | 10 | 5 | 1 | 0.25 | 0.1 |
| Matrix HQC | 0.8 | 800 | 160 | 16 | 800 | 320 | 160 | 80 | 16 | 4 | 1.6 |

Sample Preparation

Preparation of the Tape Strip Samples: Fold a tape strip in half, bisecting the white strip with adhesive side on the inside so it sticks to itself. Then fold in half again so the white strip is folded into quarters so the tape strip will fit into the 15 mL centrifuge tube with the white segment of the tape strip at the top. Tape strips can be submitted with this step already completed or they can be placed in the tube without folding.

Preparation of the Test Solution: Add 2 mL of DI water, 2 mL of $HNO_3$ and 0.05 mL of HF to the sample. Place in pre-heated hot block at 105° C. with caps on loosely. Heat the sample on the hot block for 120±10 min. Remove samples from the hot block. Pipet 0.2 mL of PG-8 and dilute to 10 mL with DI water. Cap and mix well. The tape strip will remain intact. Place on auto sampler with tape strip still in the tube (optionally, tape strip can be removed from the tube using disposable plastic spatula).

Instrument Operation

ICP-MS/MS is optimized per manufacturer's recommendation. Typical method parameters and sample introduction components are given below for the Agilent 8800 Triple Quad ICP-MS/MS.

| | |
|---|---|
| RF Power | 1600 W |
| RF Matching | 1.80 V |
| Sample Depth | 8.0 mm |
| Nebulizer | Microflow, PFA |
| Spray Chamber | PFA double-pass, Peltier-cooled |
| Nebulizer (Carrier) Gas Flow | 0.8 L/min |
| Makeup/Dilution Gas Flow | 0.4 L/min |
| Spray Chamber Temperature | 2° C. |
| Nebulizer Pump Rate | 0.1 rps |
| Sample Pump Tubing | 1.02 mm ID (white-white), PVC |
| ISIS loop | 2 mL |
| Replicates | ≥3 |
| Sweeps per Replicate | 20 |
| Scan Type | Single Quad - NG mode; MS/MS - all gas modes |
| Tune Mode Stabilization Time | No Gas [NG]: 20 sec |
| | Helium [He]: 25 sec |
| | Oxygen [O2]: 25 sec |

Detection schemes chosen for each analyte are given below, but others could be used if proper controls are put in place to ensure specificity. The isotope and cell gas mode should be documented along with the data.

| Analyte Detection Scheme | Analyte Integration Time (sec) | IS Detection Scheme | IS Integration Time (sec) |
|---|---|---|---|
| Na 23 → 23 [He] | 0.2 | Rh 103 → 103 [He] | 0.2 |
| Mg 24 → 40 [O2] | 2.0 | Ga 71 → 71 [O2] | 0.2 |
| K 39 → 39 [He] | 0.2 | Rh 103 → 103 [He] | 0.2 |
| Ca 44 → 60 Ca [O2] | 1.0 | Ga 71 → 71 [O2] | 0.2 |
| V 51 → 67 [O2] | 1.5 | Rh 103 → 103 [O2] | 0.2 |
| Cr 52 → 52 [He] | 1.0 | Rh 103 → 103 [He] | 0.2 |
| Mn 55 → 55 [He] | 1.5 | Rh 103 → 103 [He] | 0.2 |
| Fe 56 → 56 [He] | 0.2 | Rh 103 → 103 [He] | 0.2 |
| Ni 60 → 60 [He] | 1.0 | Rh 103 → 103 [He] | 0.2 |
| Cu 63 → 63 [He] | 1.0 | Rh 103 → 103 [He] | 0.2 |
| Zn 66 → 66 [He] | 1.5 | Rh 103 → 103 [He] | 0.2 |
| As 75 → 91 [O2] | 1.0 | Rh 103 → 103 [O2] | 0.2 |
| Rb 85 → 85 [He] | 1.5 | Rh 103 → 103 [He] | 0.2 |
| Sr 88 → 88 [He] | 1.0 | Rh 103 → 103 [He] | 0.2 |
| Cd 111 [NG] | 1.5 | Rh 103 [NG] | 0.2 |
| Cs 133 [NG] | 0.2 | Rh 103 [NG] | 0.2 |
| La 139 → 155 [O2] | 2.0 | Rh 103 → 103 [O2] | 0.2 |
| Sum† of Pb 208, 207, and 206 [NG] | 0.2 | Tl 205 [NG] | 0.2 |
| U 238 [NG] | 1.5 | Tl 205 [NG] | 0.2 |

†Summed through correction equation 208 = 208 + 207 + 206

Analyze calibration curve (from low to high) to build a weighted ($1/x^2$) linear regression (other regression lines are possible) plot for each analyte using the instrument software. Between each sample and standard an appropriate rinse combination should be use to clean out sample/standard between samples. Next, analyze a blank check to ensure there is no carry-over of any metal in the instrument, analyze the QC samples (CCV and ICV), QC Blank check, and QC samples. Re-analyze the CCV about every 20 samples to ensure no instrument drift and accurate results. Re-analyze CCV at the end of the analysis.

System Suitability

The correlation coefficient of the calibration curve for each element should be ≥0.995 during the initial calibration.

The precision (% RSD) of the replicate readings of the calibration standards should be ≤25% for the lowest standard, and ≤20% for all other calibration standards. The CCV and ICV QC check standards recovery should be within 80-120% of the prepared value. All sample results should be bracketed by passing QC standards. The measured value for the QC Blank Check should not exceed the value of the lowest standard. Lowest standard defines LLOQ. QC Blank Check pass/fail outcome may influence the need to increase LLOQ. The recovery of the internal standard should be within 60-140%.

Batch Suitability

The following criteria should be satisfied for each batch of samples. Method Blank value should be <LLOQ. Matrix LQC recovery should be within 75-125%, and Matrix MQC and HQC recovery should be within 80-120%. Per each analyte, 67% of all Matrix QCs and 50% at each QC level should fall within specified criteria.

TSB values should be monitored for unusually high concentration if compared to other replicates within a batch and/or to previously analyzed blanks. Variation between individual replicates of TSB is analyte-dependent. In general, if concentration is above LLOQ and falls out of pattern by exceeding expected value by a factor of 2 or more, it may be considered an outlier.

Calculations—Examples

Calibration and QC Standard Concentration $$\text{Std Conc}\left(\frac{\mu g}{mL} \text{ or ppm}\right) = \frac{\text{Stock Soln Conc}\left(\frac{\mu g}{mL}\right) * \text{Stock Soln Aliquot (mL)}}{\text{Final Soln Vol (mL)}} \quad \text{Equation 1A}$$

$$\text{Std Conc}\left(\frac{ng}{mL} \text{ or ppb}\right) = \frac{\text{Stock Soln Conc}\left(\frac{\mu g}{L}\right) * \text{Stock Soln Aliquot (mL)} * 1000\left(\frac{ng}{\mu g}\right)}{\text{Final Soln Vol (mL)} * 1000\left(\frac{mL}{L}\right)} \quad \text{Equation 1B}$$

$$\text{Std Conc}\left(\frac{ng}{mL} \text{ or ppb}\right) = \frac{\text{Stock Soln Conc}\left(\frac{\mu g}{mL}\right) * \text{Stock Soln Aliquot (mL)} * 1000\left(\frac{ng}{\mu g}\right)}{\text{Final Soln Vol (mL)}} \quad \text{Equation 1C}$$

Amount Per Tape Strip (μg or Ng)

$$m_{Sample} \text{ (}\mu g \text{ per tape strip)} = \text{Test Soln Conc}\left(\frac{\mu g}{mL}\right) * \text{Test Soln Volume (mL)} \quad \text{Equation 2A}$$

$$m_{Sample} \text{ (ng per tape strip)} = \text{Test Soln Conc}\left(\frac{ng}{mL}\right) * \text{Test Soln Volume (mL)} \quad \text{Equation 2B}$$

Matrix QC Spike Recovery $$\text{Matrix QC Spike Recovery (\%)} = \frac{\left[\text{Concentration}_{Matrix\ QC}\left(\frac{\mu g}{L} \text{ or } \frac{ng}{L}\right) - \text{Concentration}_{TSB\ Mean}\left(\frac{\mu g}{L} \text{ or } \frac{ng}{L}\right)\right]}{\text{Concentration}_{Prepared}\left(\frac{\mu g}{L} \text{ or } \frac{ng}{L}\right)} \times 100\% \quad \text{Equation 3}$$

Matrix LOC Total Analyte Recovery $$\text{Matrix LQC Total Analyte Recovery (\%)} = \frac{\text{Concentration}_{Matrix\ LQC}\left(\frac{\mu g}{L} \text{ or } \frac{ng}{L}\right)}{\left[\text{Concentration}_{Prepared}\left(\frac{\mu g}{L} \text{ or } \frac{ng}{L}\right) + \text{Concentration}_{TSB\ Mean}\left(\frac{\mu g}{L} \text{ or } \frac{ng}{L}\right)\right]} \times 100\% \quad \text{Equation 4}$$

Results

Results can be reported with a maximum of 3 significant figures. Results for Na, Mg, K, Ca and Fe can be reported in μg per tape strip, and for V, Cr, Mn, Ni, Cu, Zn, As, Rb, Sr, Cd, Cs, La, Pb and U—in ng per tape strip.

Combinations

A. A method of measuring airborne metal pollutants on skin, comprising: a) applying to the skin area of interest a tape strip having a peel force sufficient to remove skin cells from the skin when removed from the skin area; b) removing the tape strip; c) placing the tape strip in a clean container; d) digesting a target metal from the tape strip forming a tape strip digestion solution; e) digesting the target metal from a blank tape strip forming a blank tape strip digestion solution in a second clean container in the same manner as the tape strip placed on the skin, wherein the blank tape strip has not been placed on the skin; f) measuring the level of the target metal from the tape strip digestion solution using inductively coupled plasma tandem mass spectrometry; g) measuring the level of the target metal from the blank tape strip digestion solution in the same manner as the tape strip placed of the skin; and h) calculating the level of target metal from the tape strip digestion solution accounting for the level of the target metal from the blank tape strip digestion solution.

B. The method of paragraph A, further comprising marking at least a portion of the area of skin covered by the tape strip, such that additional tape strips could be placed in the same skin area.

C. The method of any of paragraphs A-B, wherein the peel force of the tape strip is 3 g/cm or more.

D. The method of any of paragraphs A-C, wherein the tape strip has a surface area of about 1 $cm^2$ to about 12 $cm^2$.

E. The method of any of paragraphs A-D, wherein the target metal comprises lead, sodium, magnesium, potassium, calcium, vanadium, chromium, manganese, iron, nickel, copper, zinc, arsenic, rubidium, strontium, cadmium, cesium, lanthanum, uranium, or a combination thereof.

F. The method of any of paragraphs A-E, wherein the tape strip is folded in half with the adhesive portion of the adhesive strip on the inside, after it is removed from the skin.

G. The method of any of paragraphs A-F, further comprising pressing the tape strip onto the skin.

H. The method of paragraph G, wherein the tape strip is pressed to the skin for 5 seconds or more.

I. The method of any of paragraphs A-H, wherein the tape strip is removed from the skin using a tool.

J. The method of paragraph I, wherein the tool is a tweezer or a forceps.

K. The method of any of paragraphs A-J, wherein the tape strip is weighed before and after removal from the skin.

L. The method of any of paragraphs A-K, wherein the tape strip is measured for optical clarity after removal from the skin.

M. The method of any of paragraphs A-L, wherein a, b, c, e, f, and h are repeated on one or more additional tape strips.

N. The method of paragraph M, wherein the additional tape strips are placed in the same clean container as the first tape strip.

O. The method of any of paragraphs A-N, wherein accounting for the level of the target metal from the digested blank tape strip comprises subtracting the level of the target metal of the blank tape strip from the level of target metal from the tape strip(s).

P. A method of measuring an airborne metal on skin, comprising: a) preparing a first skin sample from a subject for measurement of a target metal via inductively coupled plasma tandem mass spectrometry; b) preparing a second skin sample from the subject for measurement of the target metal via inductively coupled plasma tandem mass spectrometry; and c) measuring the target metal in the first and second skin samples with inductively coupled plasma tandem mass spectrometry; wherein the first skin sample is from an area of skin exposed to an airborne metal pollutant and the second skin sample is from an area of skin routinely covered by clothing.

Q. The method of paragraph P, further comprising comparing the level of the target metal in the first skin sample to the geological record to determine if the level of target metal is anthropogenically enriched.

R. The method of any of paragraphs P-Q, wherein the first and second skin samples are obtained by tape stripping, scraping, excision, or a combination thereof.

S. The method of any of paragraphs P-R, wherein the skin samples are obtained by tape stripping.

T. The method of any of paragraphs R-S, wherein the tape stripping utilizes an adhesive strip with a peel force of 3 g/cm or more.

U. The method of any of paragraphs R-T, wherein the tape stripping utilizes an adhesive strip with a surface area of about 1 cm$^2$ to about 12 cm$^2$.

V. The method of any of paragraphs R-U, further comprising measuring the level of the target metal from a blank adhesive strip in the same manner as the adhesive strip placed on the skin.

W. The method of any of paragraphs P-V, wherein the target metal comprises lead, sodium, magnesium, potassium, calcium, vanadium, chromium, manganese, iron, nickel, copper, zinc, arsenic, rubidium, strontium, cadmium, cesium, lanthanum, uranium, or a combination thereof.

X. A method of measuring airborne metal pollutants on skin, comprising: a) selecting a tape strip with a peel force sufficient to remove skin cells from the skin when removed; b) applying the tape strip to an area of skin; c) removing the tape strip with a skin sample; d) repeating a, b, and c at least 5 times utilizing a new tape strip each time on the same area of skin; e) placing each tape strip in a separate clean container; f) preparing the skin sample for measurement; g) measuring the level of a target metal in each digested skin sample with inductively coupled plasma tandem mass spectrometry; and h) correcting for any contribution from the tape strip in each sample; wherein the level of target metal in each successive tape strip can show the level of target metal penetration into the skin.

Y. The method of paragraph X, wherein preparing the skin sample for measurement comprises digesting the skin sample from each tape strip.

Z. The method of paragraph X, wherein preparing the skin sample for measurement comprises digesting the tape strip.

AA. The method of any of paragraphs X-Z, further comprising comparing the level of the target metal in the skin samples to the geological record to determine if the level of target metal is anthropogenically enriched.

BB. The method of any of paragraphs X-AA, wherein the tape strip has a peel force of 3 g/cm or more.

CC. The method of any of paragraphs X-BB, wherein the tape strip has a surface area of about 1 cm$^2$ to about 12 cm$^2$.

DD. The method of any of paragraphs X-CC, wherein correcting for the tape strip comprises measuring the level of the target metal from one or more blank tape strips in the same manner as the tape strips placed on the skin and subtracting the contribution of the blank tape strip or the average of the blank tape strips if more than one is measured; or a standard value for each tape strip where measured previously.

EE. The method of any of paragraphs X-DD, wherein the target metal comprises lead, sodium, magnesium, potassium, calcium, vanadium, chromium, manganese, iron, nickel, copper, zinc, arsenic, rubidium, strontium, cadmium, cesium, lanthanum, uranium, or a combination thereof.

FF. The method of any of paragraphs X-EE, wherein after the tape strip is placed on the skin, the skin is marked near one or more edges of the tape strip, so that subsequent tape strips can be placed in the same area.

GG. The method of any of paragraphs X-FF, wherein the tape strip is removed from the skin using a tool.

HH. The method of paragraph GG, wherein the tool is a tweezer or a forceps.

II. The method of any of claims X-HH, where a-c are repeated about 20 times or until the glistening layer is reached.

JJ. The method of any of paragraphs X-II, wherein the tape strip is placed in a container prior to a subsequent tape strip being placed on the skin.

KK. A method of identifying a skin cleanser which can reduce the amount of airborne pollution on skin, comprising: a) identifying a subject with pollution on at least a portion of the skin; b) applying a first tape strip to a skin collection site on the subject; c) removing the first tape strip with a first skin sample from the first skin collection site; d) placing the first tape strip in a container; e) washing a comparable second skin collection site with a skin cleanser; f) allowing the second skin collection site to dry; g) applying a second tape strip to the second skin collection site; h) removing the second tape strip with a second skin sample from the second skin collection site; i) placing the second tape strip in a container; j) digesting the first skin sample to form a first digestion solution and the second skin sample to form a second digestion solution; and k) measuring the level of a target metal from the first digestion solution and second digestion solution using inductively coupled plasma tandem mass spectrometry; wherein a decrease of 10% or more from the first strip to the second strip indicates the ability of the skin cleanser to remove at least a portion of the target metal from the surface of the skin.

LL. The method of paragraph KK, further comprising comparing the level of the target metal in the skin samples to the geological record to determine if the level of target metal is anthropogenically enriched.

MM. The method of any of paragraphs KK-LL, wherein the tape strips have a peel force of 3 g/cm or more.

NN. The method of any of paragraphs KK-MM, wherein the tape strips have a surface area of about 1 cm$^2$ to about 12 cm$^2$.

OO. The method of any of paragraphs KK-NN, further comprising correcting for the tape strip in the metal measurement by measuring the level of the target metal from a blank tape strip in the same manner as the tape strips placed on the skin and subtracting the value of the target metal in the blank tape strip from the value of the target metal in the skin samples.

PP. The method of any of paragraphs KK-OO, wherein the target metal comprises lead, sodium, magnesium, potassium, calcium, vanadium, chromium, manganese, iron, nickel, copper, zinc, arsenic, rubidium, strontium, cadmium, cesium, lanthanum, uranium, or a combination thereof.

QQ. The method of any of paragraphs KK-PP, wherein after the tape strips are placed on the skin, the skin is marked near one or more edges of the tape strips, so that subsequent tape strips can be placed in the same areas.

RR. The method of any of paragraphs KK-QQ, wherein the tape strips are removed from the skin using a tool.

SS. The method of paragraph RR, wherein the tool is a tweezer or a forceps.

TT. The method of any of paragraphs KK-SS, where a-k are repeated about 20 times or until the glistening layer is reached.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of identifying a skin cleanser which can reduce the amount of airborne pollution on skin, comprising:
   a) identifying a subject with pollution on at least a portion of the skin;
   b) applying a first tape strip to a skin collection site on the subject;
   c) removing the first tape strip with a first skin sample from the first skin collection site;
   d) placing the first tape strip in a container;
   e) washing a comparable second skin collection site with a skin cleanser;
   f) allowing the second skin collection site to dry;
   g) applying a second tape strip to the second skin collection site;
   h) removing the second tape strip with a second skin sample from the second skin collection site;
   i) placing the second tape strip in a container;
   j) digesting the first skin sample to form a first digestion solution and the second skin sample to form a second digestion solution; and
   k) measuring the level of a target metal from the first digestion solution and second digestion solution using inductively coupled plasma tandem mass spectrometry; wherein a decrease of 10% or more from the first strip to the second strip indicates the ability of the skin cleanser to remove at least a portion of the target metal from the surface of the skin.

2. The method of claim 1, further comprising comparing the level of the target metal in the skin samples to the geological record to determine if the level of target metal is anthropogenically enriched.

3. The method of claim 1, wherein the tape strips have a peel force of 3 g/cm or more.

4. The method of claim 1, wherein the tape strips have a surface area of about 1 cm$^2$ to about 12 cm$^2$.

5. The method of claim 1, further comprising correcting for the tape strip in the metal measurement by measuring the level of the target metal from a blank tape strip in the same manner as the tape strips placed on the skin and subtracting the value of the target metal in the blank tape strip from the value of the target metal in the skin samples.

6. The method of claim 1, wherein the target metal comprises lead, sodium, magnesium, potassium, calcium, vanadium, chromium, manganese, iron, nickel, copper, zinc, arsenic, rubidium, strontium, cadmium, cesium, lanthanum, uranium, or a combination thereof.

7. The method of claim 1, wherein after the tape strips are placed on the skin, the skin is marked near one or more edges of the tape strips, so that subsequent tape strips can be placed in the same areas.

8. The method of claim 1, wherein the tape strips are removed from the skin using a tool.

9. The method of claim 8, wherein the tool is a tweezer or a forceps.

10. The method of claim 1, wherein a-k are repeated about 20 times or until the glistening layer is reached.

\* \* \* \* \*